US007572948B2

(12) United States Patent
Martin et al.

(10) Patent No.: US 7,572,948 B2
(45) Date of Patent: Aug. 11, 2009

(54) FULVENE PURIFICATION

(75) Inventors: Joel L. Martin, Bartlesville, OK (US);
Qing Yang, Bartlesville, OK (US); Rex E. Murray, Bartlesville, OK (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 273 days.

(21) Appl. No.: 11/803,864

(22) Filed: May 16, 2007

(65) Prior Publication Data

US 2008/0287725 A1 Nov. 20, 2008

(51) Int. Cl.
*C07C 7/10* (2006.01)

(52) U.S. Cl. ................ 585/809; 585/833; 585/836; 585/837; 585/838; 585/863

(58) Field of Classification Search ........... 585/809, 585/833, 836, 837, 838, 860, 863
See application file for complete search history.

(56) References Cited

U.S. PATENT DOCUMENTS

| | | | |
|---|---|---|---|
| 3,381,017 A | 4/1968 | Waugh | |
| 4,611,024 A | 9/1986 | Wolfe | |
| 4,939,217 A | 7/1990 | Stricklen | |
| 5,001,176 A | 3/1991 | Nakazima | |
| 5,015,679 A | 5/1991 | Matumura | |
| 5,179,063 A | 1/1993 | Harris et al. | |
| 5,191,132 A | 3/1993 | Patsidis et al. | |
| 5,210,352 A | 5/1993 | Alt et al. | |
| 5,225,500 A | 7/1993 | Elder et al. | |
| 5,347,026 A | 9/1994 | Patsidis et al. | |
| 5,349,100 A * | 9/1994 | Mintz ................ 585/350 |
| 5,399,636 A | 3/1995 | Alt et al. | |
| 5,401,817 A | 3/1995 | Palackal et al. | |
| 5,420,320 A | 5/1995 | Zenk et al. | |
| 5,436,305 A | 7/1995 | Alt et al. | |
| 5,451,649 A | 9/1995 | Zenk et al. | |
| 5,496,781 A | 3/1996 | Geerts et al. | |
| 5,498,581 A | 3/1996 | Welch et al. | |
| 5,541,272 A | 7/1996 | Schmid et al. | |
| 5,554,795 A | 9/1996 | Frey et al. | |
| 5,563,284 A | 10/1996 | Frey et al. | |
| 5,565,592 A | 10/1996 | Patsidis et al. | |
| 5,571,880 A | 11/1996 | Alt et al. | |
| 5,594,078 A | 1/1997 | Welch et al. | |
| 5,631,203 A | 5/1997 | Welch et al. | |
| 5,631,335 A | 5/1997 | Alt et al. | |
| 5,654,454 A | 8/1997 | Peifer et al. | |
| 5,668,230 A | 9/1997 | Schertl et al. | |
| 5,705,478 A | 1/1998 | Boime | |
| 5,705,579 A | 1/1998 | Hawley et al. | |
| 5,744,666 A | 4/1998 | Welch et al. | |
| 6,025,512 A | 2/2000 | Crowther et al. | |
| 6,156,845 A | 12/2000 | Saito et al. | |
| 6,175,027 B1 | 1/2001 | Sullivan et al. | |
| 6,187,880 B1 | 2/2001 | Welch et al. | |
| 6,231,804 B1 | 5/2001 | Yamauchi et al. | |
| 6,291,382 B1 | 9/2001 | Koppl et al. | |
| 6,313,225 B2 | 11/2001 | Saito et al. | |
| 6,509,427 B1 | 1/2003 | Welch et al. | |
| 6,524,987 B1 | 2/2003 | Collins et al. | |
| 6,534,665 B1 | 3/2003 | Nunez et al. | |
| 7,064,225 B2 | 6/2006 | Thorn et al. | |
| 7,166,731 B2 | 1/2007 | Park et al. | |
| 2005/0288524 A1 | 12/2005 | Thorn et al. | |

OTHER PUBLICATIONS

Hudson, Richard D.A., Foxman, Bruce M., Rosenblum, Myron; Synthesis and Properties of New Stacked Metallocene Polymers; Organometallics; 1999; 4098-4106; 18; American Chemical Society, USA.

Day, J.H.; The Fulvenes, Mar. 16, 1953, 167-189, Department of Chemistry, Ohio University, Athens, Ohio, USA.

Bergmann, E.D., The Fulvenes, Progress in Organic Chemistry, 1955, pp. 81-171, 3, Academic Press Inc., New York, USA.

Gilman, H.; Gorsich, R.D.; Reactions of Lithium with Some Aromatic Hydrocarbons in Tetrahydrofuran, (Apr. 1958), 550-551, vol. 23, Chemistry Department of Iowa State College, Ames, Iowa, USA.

Yates, P., Fulvenes, Advances in Alicyclic Chemistry, (1968), pp. 60-184, vol. 2, Academic Press, New York, USA.

Xiao, Ya-Ping, et al., One Step Synthesis of Dicyclopentadienylmagnesium and its Reaction . . . , Youji Huaxue/Organic Chemistry, vol. 16, No. 5 (1996) pp. 450-452.

Stone, K.J.; Little, R.D.; an Exceptionally Simple and Efficient Method for the Preparation of a Wide Variety of Fulvenes, The Journal of Organic Chemistry, (Jun. 1, 1984), 1849-1853, vol. 49-11, American Chemical Society.

Li, J.H.; Liu, J.T.; Jiao, L.J.; Zhang, X.Q.; May, Y..D.; Zhang, N.; Reaction of Substituted Cyclopentadienyl-Magnesium-Chloride with Carbonyl Compound (I): Research in Chinese Universities, (1992), 370-376; vol. 8-4, Shandong Province, China.

Kajigaeshi, S., et al. Selective Preparation Of Fluorene Derivatives Using the t-Butyl Function As A Positional protective Group, The Chem. Society of Japan, vol. 59, p. 97 (1986).

Alt, H.G., et al., $C_1$-verbrückte Fluoryliden-Indenylidenkomplexe des Typs $(C_{13}H_8\text{-}CR_2\text{-}C_9H_6.nR'n)ZrCl_2$ ($n$=0, 1: R = Me, Ph, Butenyl; R' = Alkyl, Alkenyl) als Metallocenkatalysatorvorstufen für die Ethylenpolymerisation, Journal of Organometallic Chemistry, vol. 562, pp. 153-181 (1998).

(Continued)

*Primary Examiner*—Tam M Nguyen
(74) *Attorney, Agent, or Firm*—Merchant & Gould, P.C.

(57) ABSTRACT

The present invention provides a method of removing undesired isomers, including substituted cyclopentadiene regioisomers, from the desired fulvene in a crude fulvene composition by selectively reacting the undesired isomers with pyrrolidine and 4-(N,N-dimethylamino)benzaldehyde. This reaction converts the undesired substituted cyclopentadienes into fulvene-type compounds that is readily separated from the desired fulvene.

22 Claims, 3 Drawing Sheets

OTHER PUBLICATIONS

Alt, H.G., et al., $C_1$-Bridged fluorenylidene cyclopentadienylidene complexes of the type $(C_{13}H_8\text{-}CR^1R^2\text{-}C_5H_3R)ZrCl_2$ ($R^1$, $R^2$ = alkyl, phenyl, alkenyl; R = H, alkyl, alkenyl, substituted silyl) as catalyst precursors for the polymerization of ethylene and propylene, Journal of Organometallic Chemistry, vol. 568, pp. 87-112 (1998).

Koppl, A., et al., "Heterogeneous Metallocene Catalysts for Ethylene Polymerization," Journal of Molecular Catalysis A: Chemical, vol. 165, pp. 23-32 (2001).

Duff, Hitchcock, Lappert, and Taylor, Journal Organometallic Chemistry, (1985), 293, 271-283.

Alt, et al., Syndiospezifische Polymerisation von Propylen: 2- und 2, 7-substituierte Metallocenkomplex des Typs $(C_{13}H_8\text{-}nRnCR'_2C_5H_4)$ $MCl_2$ ($n$=1,2; R=Alkoxy, Alkyl, Aryl, Hal; R'=Me, Ph; M=Zr, Hf), Journal of Organometallic Chemistry, vol. 522 (1996), pp. 39-54.

Fierro, et al., Synthesis and Characterization of New One-Carbon-Bridged Titanocene and Zirconocene Derivatives, Journal of Organometallic Chemistry, vol. 485 (1995), pp. 11-17.

Stille, et al., Intramolecular Diels-Alder Reaction of α,β-Unsaturated Ester Dienophiles with Cyclopentadiene and the Dependence on Tether Length, Journal Org. Chem., vol. 54, No. 2 (1989), pp. 434-444.

* cited by examiner

FULVENE PURIFICATION

TECHNICAL FIELD OF THE INVENTION

This invention relates to the field of organic synthesis, including chemistry that is useful for the preparation and purification of fulvenes, and use of the purified fulvenes in the synthesis of bis(cyclopentadienyl)alkanes and ansa-metallocenes.

BACKGROUND OF THE INVENTION

Metallocenes constitute useful catalysts for olefin polymerization when combined with a cocatalyst such as an aluminoxane. It is generally accepted that the properties of the polymers formed using such catalyst combinations are determined in large part by the structural nature of the metallocene, including the steric and electronic features imparted to the complex by its cyclopentadienyl ligands. Therefore, there is a continuing need to develop improved methods for preparing metallocenes and their precursor ligands that allow for a range of diverse substituents to be incorporated into the ligand structure. There is also a need for improved methods for preparing metallocenes that provide the desired compounds as well as their precursor ligands in higher yield and/or greater purity.

One step in the preparation of certain metallocenes is the isolation of an intermediate fulvene. Fulvenes have the general formula $C_4R''_4C=CRR'$ and the following structure:

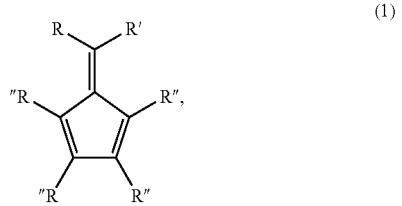

(1)

wherein R, R', and R'' are generally and independently hydrocarbyl or hydrogen. As precursors to cyclopentadienyl ligands and metallocene compounds, fulvenes can provide a means for integrating a range of substituents into the metallocene structure. One aspect of this utility can be seen from the reaction of fulvenes with anionic cyclopentadienyl (Cp), indenyl (Ind), or fluorenyl (Flu) reagents as illustrated in Scheme 1, because the resulting products can be used as ligand precursors to form bridged or ansa-metallocenes. Ansa-metallocene catalysts are useful in olefin polymerizations in part because of the impact the tailored ligand set can have on the properties of the resulting polymer.

Scheme 1

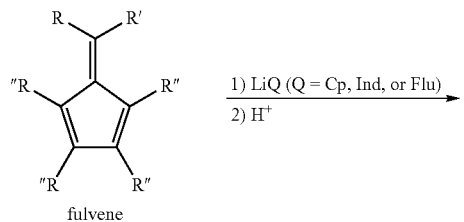

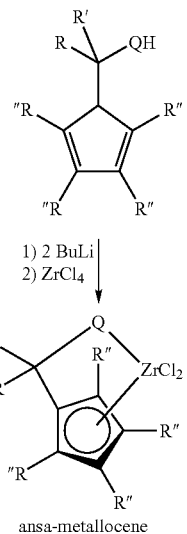

ansa-metallocene

Therefore, it is of interest to develop new methods to prepare fulvenes that may provide these ligands in higher yields, greater selectively, and/or greater purity. It is also of interest to develop new methods to prepare ansa-metallocenes based on new fulvene synthetic methods.

SUMMARY OF THE INVENTION

This invention encompasses methods for purifying a fulvene composition to afford a substantially pure fulvene, which can then be employed in the synthesis of bis($\eta^5$-cycloalkadienyl)-type ligands and metallocene complexes. This purification process can be useful when the fulvene is prepared by any method, including methods that are considered relatively selective. The substantially pure, isolated fulvenes are particularly utilitarian in preparing "tightly-bridged" ansa-metallocenes, meaning that the two $\eta^5$-cycloalkadienyl-type ligands of the metallocene are connected by a bridging group wherein the shortest link of the bridging group between the $\eta^5$-cycloalkadienyl-type ligands is a single atom.

Methods of preparing fulvenes having the general formula $C_4R''_4C=CRR'$ (1), wherein R, R', and R'' are generally and independently hydrocarbyl or hydrogen, include the reaction of a ketone $O=CRR'$ with an anionic cyclopentadienyl reagent such as $Li[C_5R''_4H]$ or $Na[C_5R''_4H]$, typically in alcoholic solvents, or in ethereal solvents followed by reaction with a proton source. This synthetic procedure often generates varying amounts of undesired regioisomers including substituted cyclopentadienes, along with the desired fulvene, thereby rendering isolation, purification, and subsequent use of the desired fulvene isomer tedious and difficult. When magnesium cyclopentadienyl reagents such as Grignard reagents are employed in this reaction, the desired fulvene compound can be formed in large excess over the undesired isomer, however isomer formation still occurs under some conditions. This magnesium cyclopentadienyl method is disclosed in U.S. Pat. Application Publication No. 2005/0288524, which is incorporated herein by reference in its entirety. Because starting with very pure fulvene greatly simplifies the subsequent fulvene reaction with anionic cyclopentadienyl (Cp), indenyl (Ind), or fluorenyl (Flu) reagents as illustrated in Scheme 1, any procedure which allows purification of the fulvene, even from Grignard reactions described above, are of interest.

Thus, in one aspect, the present invention provides a method of removing undesired isomers, including substituted cyclopentadiene regioisomers, from the desired fulvene in a crude fulvene composition by selectively reacting the undesired isomers with pyrrolidine and 4-(N,N-dimethylamino) benzaldehyde. This reaction converts the undesired substituted cyclopentadienes into a fulvene-type compound that is readily separated from the desired fulvene. In this aspect, for example, this disclosure provides a method of isolating a fulvene from a composition comprising the fulvene and at least one cyclopentadiene-containing impurity, comprising:

a) contacting the composition with 4-(N,N-dimethylamino)benzaldehyde, pyrrolidine, and optionally a first solvent to provide a first mixture;
b) contacting the first mixture with an aqueous acid to provide a second mixture;
c) extracting the second mixture with a second solvent to provide an extract, optionally concentrating the extract, and optionally drying the extract; and
d) isolating the fulvene from the extract by chromatography;

wherein:
the fulvene has the formula $C_4R^3{}_4C{=}CR^1R^2$ and the structural formula

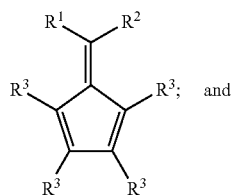

$R^1$, $R^2$, and $R^3$, in each occurrence, are independently a hydrocarbyl group having up to 20 carbon atoms, or hydrogen.

This purification procedure can be employed in any of several fulvene synthetic methods. For example, in this aspect, this disclosure provides a method of making a fulvene having the formula $C_4R^6{}_4C{=}CR^4CH_2R^5$, and the structural formula

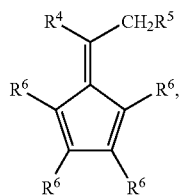

comprising:
a) contacting in an aprotic first solvent a ketone of the formula $O{=}CR^4CH_2R^5$ and a cyclopentadienyl compound selected from $Mg(C_5R^6{}_4H)X$, $Mg(C_5R^6{}_4H)_2$, or a combination thereof, to provide a first mixture;
b) contacting the first mixture with a proton source, to form a fulvene composition comprising the fulvene and optionally at least one cyclopentadiene-containing impurity;
c) contacting the fulvene composition with 4-(N,N-dimethylamino)-benzaldehyde, pyrrolidine, and optionally a second solvent to provide a second mixture;

d) contacting the second mixture with an aqueous acid to provide a third mixture;
e) extracting the third mixture with a third solvent to provide an extract, optionally concentrating the extract, and optionally drying the extract; and
f) isolating the fulvene from the extract by chromatography;

wherein:
$R^4$ is an aryl or substituted aryl group having up to 20 carbon atoms;
$R^5$ is a hydrocarbyl or substituted hydrocarbyl group having up to 20 carbon atoms, or hydrogen;
$R^6$, in each instance, is independently selected from a hydrocarbyl or substituted hydrocarbyl group having up to 20 carbon atoms, or hydrogen; and
X is Cl, Br, or I.

The purification procedure disclosed herein can also be employed in any of several bis(cyclopentadienyl)-type ligand syntheses, including bis(cyclopentadienyl), cyclopentadienyl-indenyl, and cyclopentadienyl-fluorenyl type ligands. For example, in another aspect, this disclosure provides a method of making a compound having the formula $C_4R^6{}_4CHCR^4(CH_2R^5)(QH)$ and the structural formula

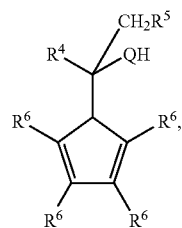

comprising:
a) contacting in an aprotic first solvent a ketone of the formula $O{=}CR^4CH_2R^5$ and a cyclopentadienyl compound selected from $Mg(C_5R^6{}_4H)X$, $Mg(C_5R^6{}_4H)_2$, or a combination thereof, to provide a first mixture;
b) contacting the first mixture with a proton source, to form a fulvene composition comprising the fulvene and optionally at least one cyclopentadiene-containing impurity;
c) contacting the fulvene composition with 4-(N,N-dimethylamino)-benzaldehyde, pyrrolidine, and optionally a second solvent to provide a second mixture;
d) contacting the second mixture with an aqueous acid to provide a third mixture;
e) extracting the third mixture with a third solvent to provide an extract, optionally concentrating the extract, and optionally drying the extract; and
f) isolating the fulvene from the extract by chromatography;
g) contacting the fulvene with MQ, followed by a proton source, to form $C_4R^6{}_4CHCR^4(CH_2R^5)(QH)$, wherein M is Li, Na, K, MgX, $Mg_{0.5}$, and wherein Q is a cyclopentadienyl, an indenyl, a fluorenyl, or a substituted analog thereof, wherein $R^4$ is an aryl or substituted aryl group having up to 20 carbon atoms;
$R^5$ is a hydrocarbyl or substituted hydrocarbyl group having up to 20 carbon atoms, or hydrogen;
$R^6$, in each instance, is independently selected from a hydrocarbyl or substituted hydrocarbyl group having up to 20 carbon atoms, or hydrogen; and X is Cl, Br, or I.

These and other features, aspects, embodiments, and advantages of the present invention will become apparent after a review of the following detailed description of the disclosed features.

The following publication and patent are incorporated herein by reference in their entireties: U.S. Patent Application Publication No. 2005/0288524; and U.S. Pat. No. 7,064,225.

DETAILED DESCRIPTION OF THE INVENTION

Figure 1:
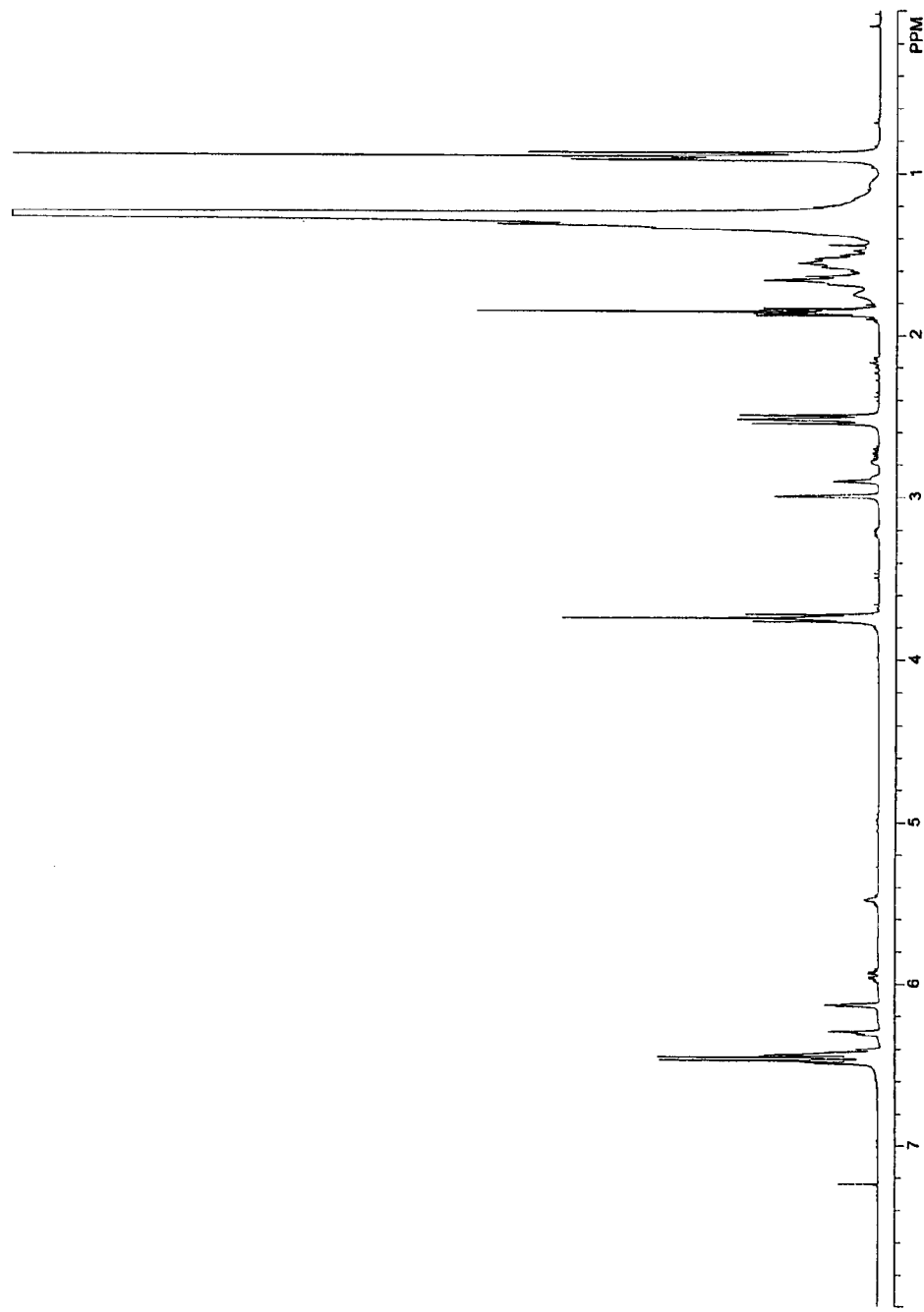
FIG. 1 illustrates the $^1$H NMR spectrum of the crude reaction product isolated from the reaction of CpMgCl and pentatriacontanone in tetrahydrofuran (THF).

The present invention provides, among other things, a method of purifying fulvenes, including a method of removing undesirable regioisomers from the desired fulvene in a crude fulvene composition. In one aspect, the disclosed method includes selectively reacting these undesirable regioisomers with pyrrolidine and 4-(N,N-dimethylamino)benzaldehyde, according to the method disclosed in *J. Org. Chem.* 1984, 49, 1849-1853, and in *Organometallics* 1999, 18, 4098-4106, both of which are incorporated herein by reference in their entireties. In this aspect, for example, this disclosure provides a method of isolating a fulvene from a composition comprising the fulvene and at least one cyclopentadiene-containing impurity, comprising:
  a) contacting the composition with 4-(N,N-dimethylamino)benzaldehyde, pyrrolidine, and optionally a first solvent to provide a first mixture;
  b) contacting the first mixture with an aqueous acid to provide a second mixture;
  c) extracting the second mixture with a second solvent to provide an extract, optionally concentrating the extract, and optionally drying the extract; and
  d) isolating the fulvene from the extract by chromatography;

wherein:
the fulvene has the formula

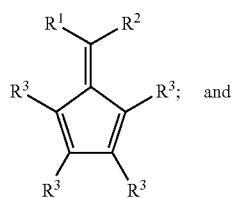; and $R^1$, $R^2$, and $R^3$, in each occurrence, are independently a hydrocarbyl group having up to 20 carbon atoms, or hydrogen.

While not intending to be bound by theory, Scheme 2 illustrates some of the cyclopentadiene-containing impurities that may be present in a fulvene composition. Specifically, Scheme 2 illustrates undesired isomers 4 and 5 that can form along with the desired fulvene 2 in a typical fulvene synthesis step, arising from different regiochemistries of dehydration of the intermediate alcohol 3. The presence of substituted cyclopentadienes 4 and 5 can be problematic during the ligand preparation illustrated in Scheme 1, because the reaction of the fulvene composition with nucleophilic cyclopentadienyl (Cp), indenyl (Ind), or fluorenyl (Flu) reagents can result in the nucleophile simply deprotonating 4 and 5 and become unavailable for the desired reaction with fulvene.

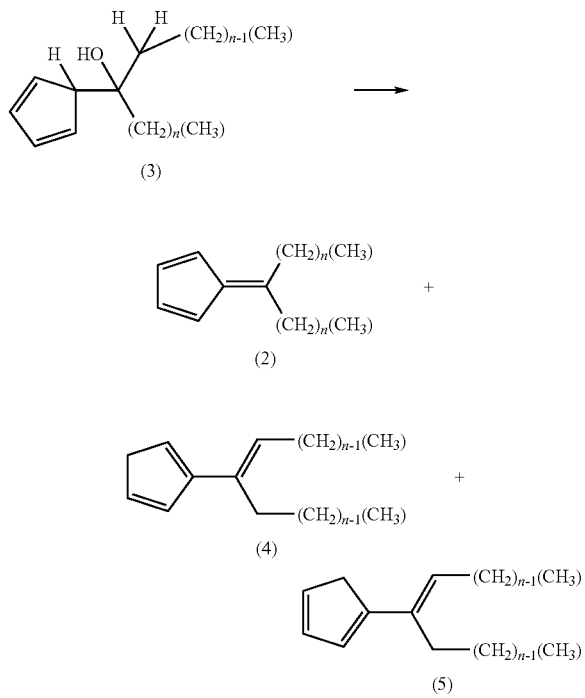

Scheme 2

Again, while not intending to be bound by theory, in one aspect, this disclosure provides a method of separating the desired fulvene 2 from the undesired cyclopentadiene-containing impurities such as 4 and 5 by selectively reacting the undesired isomers to form a product that is easily separated from fulvene 2. Thus, in one aspect, this invention provides methods of reacting these undesired regioisomers with pyrrolidine and 4-(N,N-dimethylamino)benzaldehyde to form another substituted fulvene 6, illustrated in Scheme 3, which is readily separated from the desired fulvene by chromatographic or other standard separation methods.

Scheme 3

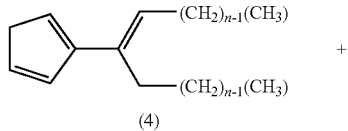

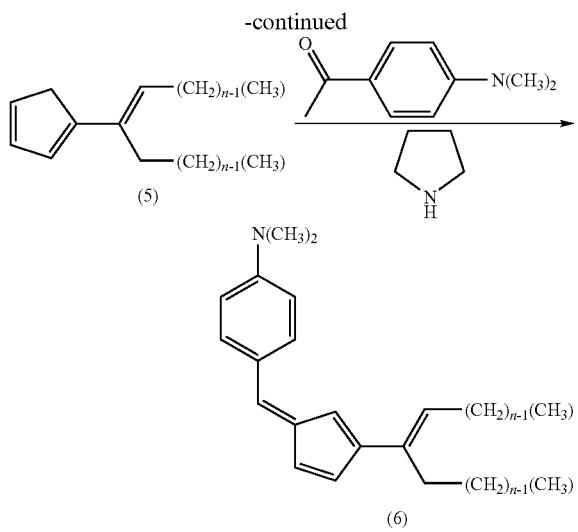

The Examples and the Figures provided herein illustrate various aspects of this invention. The preparation of 6,6-diheptadecylpentafulvene from the reaction of pentatriacontanone, ($[CH_3(CH_2)_{16}]_2CO$) and CpMgCl in THF is provided in Example 1. The $^1H$ NMR spectrum of FIG. 1 illustrates that the crude product is a mixture of the desired 6,6-diheptadecylpentafulvene and isomeric alkenylcyclopentadienes, where the presence of the undesired substituted cyclopentadiene isomers is seen by the $^1H$ NMR resonances near 3 ppm, arising from the two hydrogen atoms bonded to the same carbon atom of the cyclopentadiene ring. The two resonances indicate the presence of two isomers in different amounts.

Figure 2:
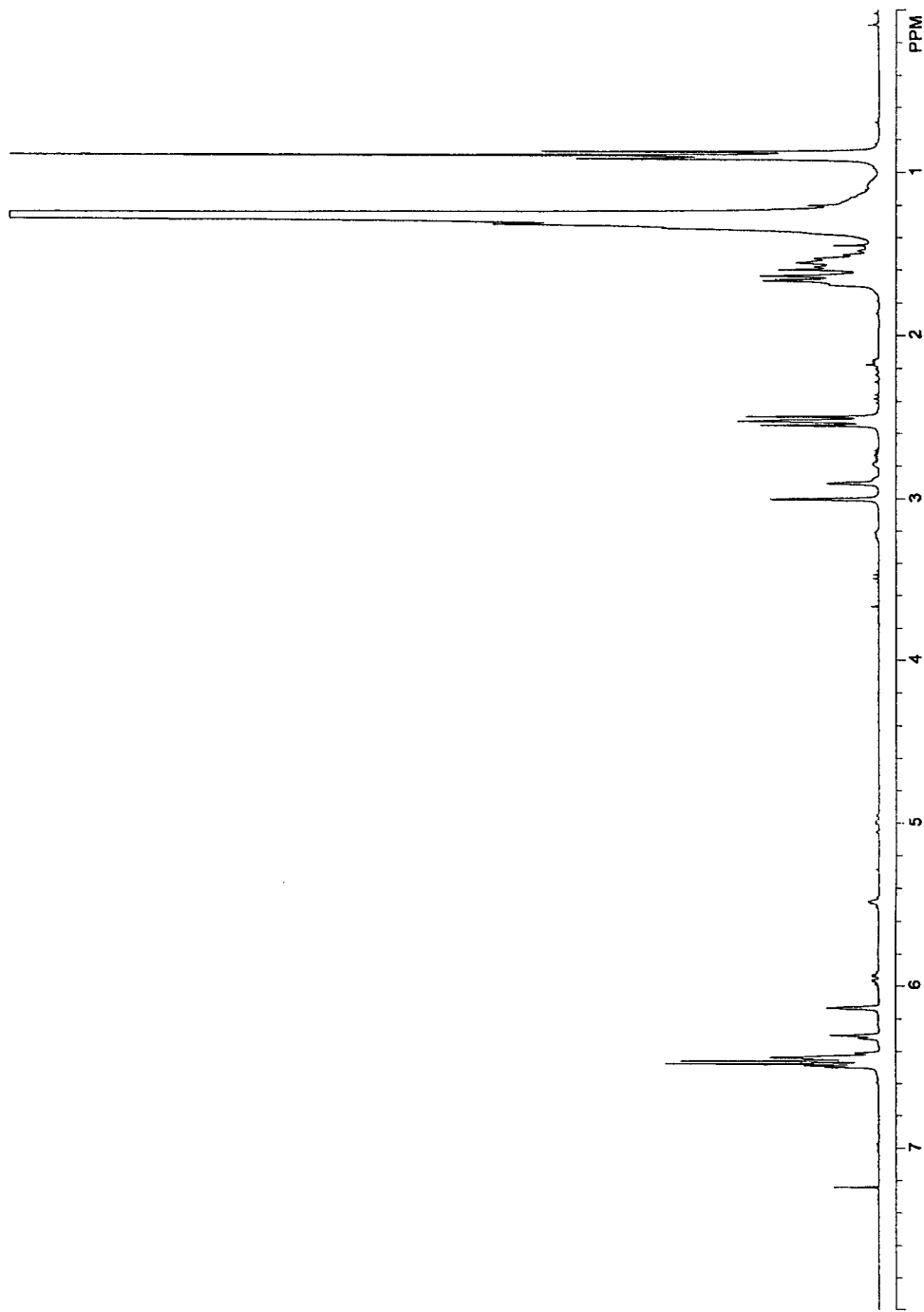
FIG. 2 illustrates the $^1$H NMR spectrum of the product isolated from the reaction of CpMgCl and pentatriacontanone in tetrahydrofuran (THF), following chromatography over silica (n-pentane eluent) prior to obtaining the spectrum.

Example 2 and FIG. 2 disclose the results of attempting to purify the 6,6-diheptadecylpentafulvene from Example 1 using standard chromatographic methods. FIG. 2 illustrates the $^1H$ NMR spectrum of the product arising from the reaction of CpMgCl and pentatriacontanone in tetrahydrofuran (THF), following chromatography over silica (n-pentane eluent) prior to obtaining the spectrum, which is seen to remove the residual THF only and is not effective in removing the isomeric alkenylcyclopentadienes.

Figure 3:
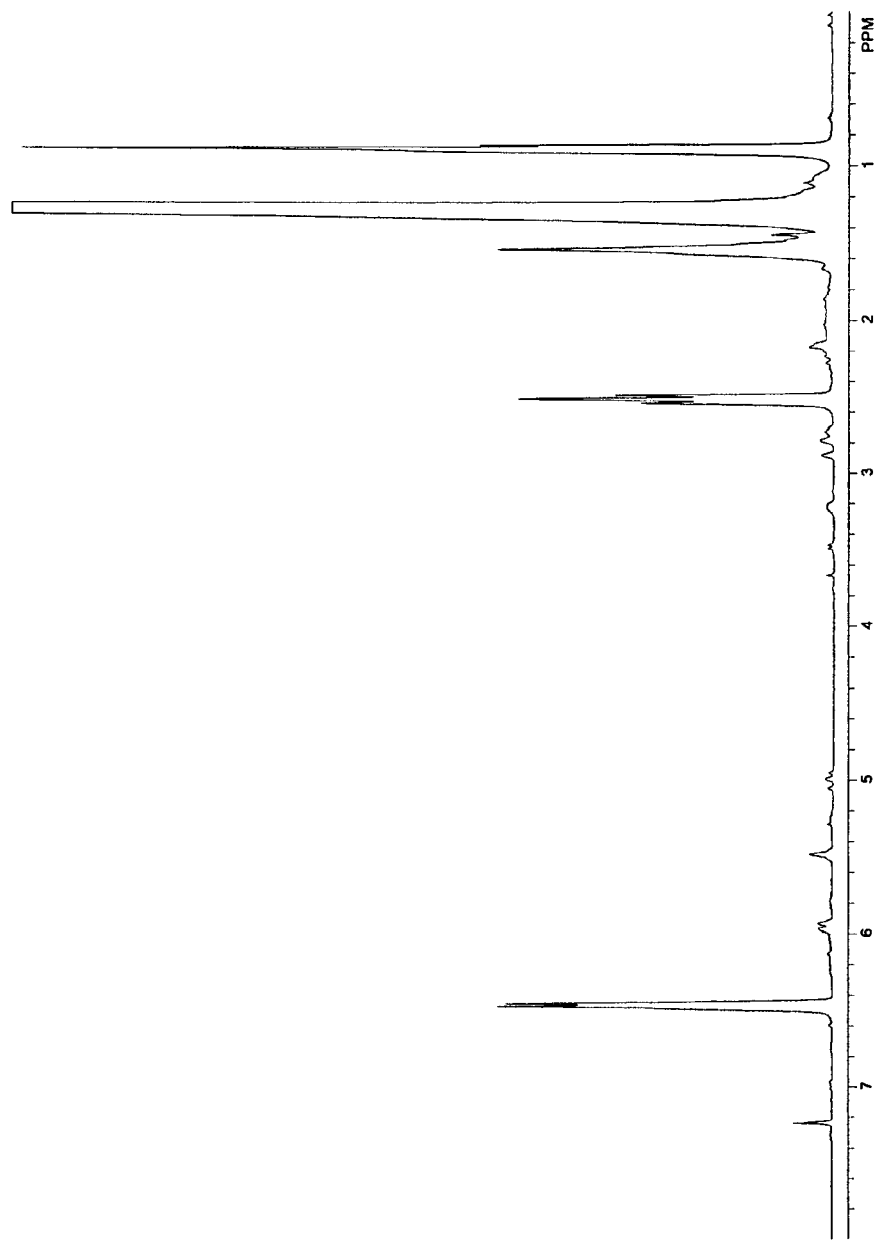
FIG. 3 illustrates the $^1$H NMR spectrum of the product arising from the reaction of CpMgCl and pentatriacontanone in tetrahydrofuran (THF), in which the crude reaction product was reacted with 4-(N,N-dimethylamino)benzaldehyde/pyrrolidine according to this disclosure, following chromatography over silica (n-pentane eluent) prior to obtaining the spectrum.

Example 3 and FIG. 3 illustrate the purification of 6,6-diheptadecylpentafulvene according to the present invention. FIG. 3 illustrates the $^1H$ NMR spectrum of the pure 6,6-diheptadecylpentafulvene product arising from the reaction of CpMgCl and pentatriacontanone in THF, in which the crude reaction product was reacted with 4-(N,N-dimethylamino)benzaldehyde/pyrrolidine, following chromatography over silica (n-pentane eluent) prior to obtaining the spectrum. Thus, the crude reaction product was reacted with 4-(N,N-dimethylamino)benzaldehyde in a mixture of methylene chloride and methanol, using pyrrolidine according to the method of Stone and Little (*J. Org. Chem.* 1984, 49, 1849-1853), which resulted in a dark red viscous liquid. The red mixture was easily separated by chromatography over silica using n-pentane to elute the pure, yellow fulvene compound, while the dark red derivative of the side products remained on the column In still another aspect, this invention provides a method of isolating a fulvene from a composition comprising the fulvene and at least one cyclopentadiene-containing impurity, as disclosed above, wherein the fulvene has the formula $C_4R^3_4C=CR^1R^2$ and the structural formula

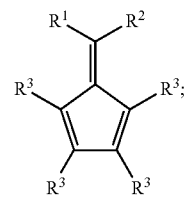

and wherein $R^1$ and $R^2$ can be selected independently from: a) a linear or a branched alkyl group; b) a linear or a branched alkenyl group; c) an aryl group; or d) an aryl-substituted linear or branched alkyl group; any of which having up to 20 carbon atoms. Moreover, another aspect of this invention provides that $R^1$ and $R^2$ are, independently, an alkyl group having from 1 to 18 carbon atoms. In another aspect, $R^3$, in each occurrence, can be selected independently from: a) a linear or a branched alkyl group having up to 12 carbon atoms; or b) hydrogen.

Yet another aspect of this invention provides that the fulvene can have the formula:

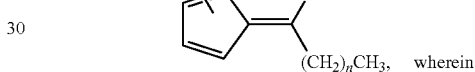

$R^3$, in each occurrence, is independently a linear or a branched alkyl group having up to 6 carbon atoms; m is 0, 1, 2, 3, or 4; and n is an integer from 1 to 16. In a related aspect, the fulvene can have the formula illustrated immediately above, wherein $R^3$, in each occurrence, is independently a linear or a branched alkyl group having up to 6 carbon atoms; m is 0, 1, 2, 3, or 4; and n is an integer from 6 to 16. Further, the desired fulvene according to the present invention can also have the formula $C_4H_4C=C[(CH_2)_{16}CH_3]_2$.

An additional aspect of this invention provides that the at least one cyclopentadiene-containing impurity can be

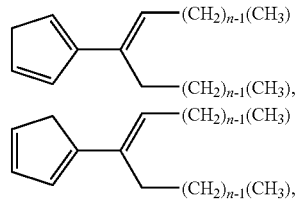

or a combination thereof, wherein n is an integer from 1 to 16. In a related aspect, this disclosure provides that the at least one cyclopentadiene-containing impurity can be

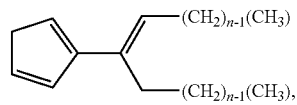

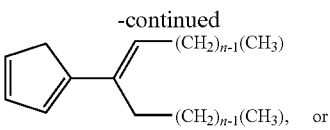

a combination thereof, wherein n is an integer from 6 to 16. An additional aspect of this invention provides that the at least one cyclopentadiene-containing impurity can be

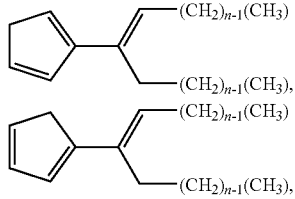

or a combination thereof.

In yet another aspect of the invention, the method of isolating a fulvene from a composition comprising the fulvene and at least one cyclopentadiene-containing impurity, comprising:
  a) contacting the composition with 4-(N,N-dimethylamino)benzaldehyde, pyrrolidine, and optionally a first solvent to provide a first mixture;
  b) contacting the first mixture with an aqueous acid to provide a second mixture;
  c) extracting the second mixture with a second solvent to provide an extract, optionally concentrating the extract, and optionally drying the extract; and
  d) isolating the fulvene from the extract by chromatography;

wherein the fulvene has the formula $C_4R^3{}_4C$=$CR^1R^2$ wherein $R^1$, $R^2$, and $R^3$ can be as disclosed herein, and wherein the first solvent can be a mixture of methylene chloride and an alcohol having up to 4 carbon atoms. Further to this aspect, the first solvent can be a mixture of methylene chloride and methanol. Moreover, another aspect of this invention provides that the second solvent can be an alkane having up to about 12 carbon atoms, including, but not limited to, pentane, hexane, heptane, or any combination thereof.

In yet another aspect of this invention, this disclosure provides that the aqueous acid employed in contacting the first mixture to provide a second mixture can be any aqueous acid, including organic acids or inorganic acids. The acid can also be a weak aqueous acid or a strong aqueous acid. Thus, useful acids can be selected from, but are not limited to, acetic acid, trifluoroacetic acid, formic acid, hydrochloric acid, phosphoric acid, sulfuric acid, nitric acid, or any combination thereof. The aqueous acid can also be ammonium salts including aqueous solutions of ammonium salts, and the like.

Still other aspects of this invention can be seen in the isolation of the fulvene from the extract, according to the present disclosure. Thus, the isolation of the purified fulvene from the extract can be accomplished by any method as would be recognized by one of ordinary skill, which is typically, but not limited to, chromatography. For example, depending on the particular substituents on the fulvene, a solid fulvene compound could be formed and purified by crystallization from solution according methods understood by one of ordinary skill in the art. When the fulvene is isolated from the extract by chromatography, the extract can be concentrated, dried, or both prior to chromatography if desired.

The purification procedure disclosed herein can be employed in any of several fulvene synthetic methods, including, but not limited to the reaction of a ketone O=CRR' with an anionic cyclopentadienyl reagent such as $Li[C_5R''_4H]$ or $Na[C_5R''_4H]$, typically in alcoholic solvents, or in ethereal solvents followed by reaction of the resulting mixture with a proton source. For example, in this aspect, this disclosure provides a method of making a fulvene having the formula $C_4R^6{}_4C$=$CR^4CH_2R^5$, and the structural formula

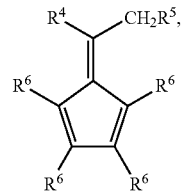

comprising:
  a) contacting in an aprotic first solvent a ketone of the formula O=$CR^4CH_2R^5$ and a cyclopentadienyl compound selected from $Mg(C_5R^6{}_4H)X$, $Mg(C_5R^6{}_4H)_2$, or a combination thereof, to provide a first mixture;
  b) contacting the first mixture with a proton source, to form a fulvene composition comprising the fulvene and optionally at least one cyclopentadiene-containing impurity;
  c) contacting the fulvene composition with 4-(N,N-dimethylamino)-benzaldehyde, pyrrolidine, and optionally a second solvent to provide a second mixture;
  d) contacting the second mixture with an aqueous acid to provide a third mixture;
  e) extracting the third mixture with a third solvent to provide an extract, optionally concentrating the extract, and optionally drying the extract; and
  f) isolating the fulvene from the extract by chromatography;

wherein:
  $R^4$ and $R^5$ are, independently, a hydrocarbyl or substituted hydrocarbyl group having up to 20 carbon atoms, or hydrogen;
  $R^6$, in each occurrence, is independently selected from a hydrocarbyl or substituted hydrocarbyl group having up to 20 carbon atoms, or hydrogen; and
  X is Cl, Br, or I.

Thus, in one aspect of the method of preparing a fulvene having the formula $C_4R^6{}_4C$=$CR^4CH_2R^5$ disclosed herein, $R^4$ and $R^5$ can be, independently, an alkyl, aryl, alkenyl, or a substituted analog thereof, having up to 20 carbon atoms, or hydrogen. Further, $R^5$ can be an alkyl or alkenyl having from 3 to 10 carbon atoms. In further aspects of the preparation of a fulvene $C_4R^6{}_4C$=$CR^4CH_2R^5$ disclosed herein, $CH_2R^5$ can be:
  $(CH_2)_xCH_3$, wherein x is an integer from 1 to 10;
  $(CH_2)_yCH$=$CH_3$, wherein y is an integer from 1 to 10;
  $CH_2CH_2C(CH_3)$=$CH_2$;
  $CH_2CH_2CH$=$C(CH_3)_2$;
  $CH_2C_6H_5$;
  $CH_2C_6H_{z-5}Me_z$, wherein z is an integer from 0 to 3;
  $CH_2C_6H_4(C_6H_{11})$;
  $CH_2C_6H_4(C_6H_5)$;
  $CH_2C_6H_4(C_4H_9)$; or a substituted analog thereof having up to 20 carbon atoms.

In other aspects of the preparation of a fulvene $C_4R^6{}_4C=CR^4CH_2R^5$ disclosed herein, the cyclopentadienyl compound can be, but is not limited to, $Mg(C_5H_5)Cl$, $Mg(C_5H_5)Br$, or a combination thereof. Moreover, for the typical cyclopentadienyl compound is $Mg(C_5H_5)X$ wherein X is Cl or Br, the molar ratio of $Mg(C_5H_5)X$ to ketone can be greater than 1. In a further aspect, the molar ratio of $Mg(C_5H_5)X$ to ketone can be greater than 1.2, or the molar ratio of $Mg(C_5H_5)X$ to ketone can be greater than 1.5.

In yet further aspects of the preparation of a fulvene $C_4R^6{}_4C=CR^4CH_2R^5$ disclosed herein, the first aprotic solvent is dimethyl ether, diethyl ether, diisopropyl ether, di-n-propyl ether, di-n-butyl ether, methyl t-butyl ether, diphenyl ether, THF, 1,2-dimethoxyethane, or any combination thereof. The second solvent can be a mixture of methylene chloride and an alcohol having up to 4 carbon atoms, for example, the second solvent can be a mixture of methylene chloride and methanol. Moreover, another aspect of this invention provides that the third solvent can be an alkane having up to about 12 carbon atoms, including, but not limited to, pentane, hexane, heptane, or any combination thereof.

Thus, in another aspect of the method of preparing a fulvene $C_4R^6{}_4C=CR^4CH_2R^5$ disclosed herein, the proton source can be any compound or combination of compounds that can serve as a source of protons to the formal anion formed upon reacting the ketone with the cyclopentadienyl reagent. In this aspect, for example, the proton source can be water, an acid including an aqueous acid, ammonium salts including aqueous solutions of ammonium salts, and the like. For example, aqueous HCl can be used as the proton source in this reaction.

In yet another aspect of the method of preparing a fulvene $C_4R^6{}_4C=CR^4CH_2R^5$, this disclosure provides that the aqueous acid employed in contacting the second mixture to provide a third mixture can be any aqueous acid, including organic acids or inorganic acids. The acid can also be a weak aqueous acid or a strong aqueous acid. Thus, useful acids can be selected from, but are not limited to, acetic acid, trifluoroacetic acid, formic acid, hydrochloric acid, phosphoric acid, sulfuric acid, nitric acid, or any combination thereof. The aqueous acid can also be ammonium salts including aqueous solutions of ammonium salts, and the like.

Still other aspects of this invention can be seen in the isolation of the fulvene from the extract, according to the present disclosure. Thus, the isolation of the purified fulvene from the extract can be accomplished by any method as would be recognized by one of ordinary skill, which is typically, but not limited to, chromatography, in the manner disclosed above for purifying the fulvene. Thus, for example, when the fulvene is isolated from the extract by chromatography, the extract can be concentrated, dried, or both prior to chromatography if desired. Depending on the particular substituents on the fulvene, a solid fulvene compound could be purified according to this disclosure, that could be crystallized from solution according methods understood by one of ordinary skill in the art.

As recognized by one of ordinary skill, when the fulvene is isolated by chromatography, any suitable chromatographic support can be employed, as this step is not limited to a specific type of solid support. Rather a large number of supports are available and are known to one skilled in the art. Solid supports include, but are not limited to, silica gels, resins, derivatized plastic films, glass beads, cotton, plastic beads, polystyrene beads, alumina gels, polysaccharides, and the like. For example, suitable chromatographic supports include silica, alumina, silica-alumina, aluminum phosphate, titania, silica-titania, zirconia, zinc oxide, mixed oxides thereof, or any mixture thereof.

The present invention also encompasses a method of synthesizing compounds comprising cyclopentadienyl-type moieties that are linked by a $>CR^1(CH_2R^2)$ group, namely bis(cyclopentadienyl)methane compounds, and various analogs thereof such as (cyclopentadienyl)(indenyl)methane and (cyclopentadienyl)(fluorenyl)methane compounds. Thus, in still a further aspect of the present invention provides a method of making a compound having the formula $C_4R^6{}_4CHCR^4(CH_2R^5)(QH)$ and the structure

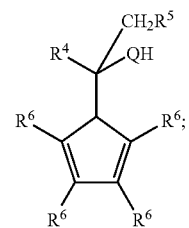

comprising:
a) contacting in an aprotic first solvent a ketone of the formula $O=CR^4CH_2R^5$ and a cyclopentadienyl compound selected from $Mg(C_5R^6{}_4H)X$, $Mg(C_5R^6{}_4H)_2$, or a combination thereof, to provide a first mixture;
b) contacting the first mixture with a proton source, to form a fulvene composition comprising the fulvene and optionally at least one cyclopentadiene-containing impurity;
c) contacting the fulvene composition with 4-(N,N-dimethylamino)-benzaldehyde, pyrrolidine, and optionally a second solvent to provide a second mixture;
d) contacting the second mixture with an aqueous acid to provide a third mixture;
e) extracting the third mixture with a third solvent to provide an extract, optionally concentrating the extract, and optionally drying the extract; and
f) isolating the fulvene from the extract by chromatography;
g) contacting the fulvene with MQ followed by a proton source, to form $C_4R^6{}_4CHCR^4(CH_2R^5)(QH)$, wherein M is Li, Na, K, MgX, or $Mg_{0.5}$, and wherein Q is a cyclopentadienyl, an indenyl, a fluorenyl, or a substituted analog thereof, wherein $R^4$ and $R^5$ are, independently, a hydrocarbyl or substituted hydrocarbyl group having up to 20 carbon atoms, or hydrogen;

$R^6$, in each occurrence, is independently selected from a hydrocarbyl or substituted hydrocarbyl group having up to 20 carbon atoms, or hydrogen; and X is Cl, Br, or I.

In this aspect, when Q is selected from a substituted cyclopentadienyl, a substituted indenyl, or a substituted fluorenyl, any substituent on Q can be selected independently from $R^{4A}$, wherein $R^{4A}$ can be an aliphatic or substituted aliphatic group having from 1 to about 20 carbon atoms, or hydrogen. Any possible substituents on $R^4$, $R^5$, $R^6$, or $R^{4A}$ are disclosed herein.

Also in this aspect of this invention, the preparation and isolation of the fulvene is disclosed above. The additional steps in synthesizing $C_4R^6{}_4CHCR^4(CH_2R^5)(QH)$ include, for example, contacting the fulvene with MQ followed by a proton source, to form $C_4R^6{}_4CHCR^4(CH_2R^5)(QH)$, wherein M is Li, Na, K, MgX (X is Cl, Br, or I), or Mg$_{0.5}$, and wherein Q is a cyclopentadienyl, an indenyl, a fluorenyl, or a substituted analog thereof. The methods and details of these preparative steps are disclosed in U.S. Patent Application Publication No. 2005/0288524, and entirety of which is incorporated herein by reference.

Numerous processes to prepare and use metallocene-based catalyst that can be employed with ligands such as C$_4$R$^6_4$CHCR$^4$(CH$_2$R$^5$)(QH) that is disclosed in this invention have been reported. For example, U.S. Pat. Nos. 4,939,217, 5,191,132, 5,210,352, 5,347,026, 5,399,636, 5,401,817, 5,420,320, 5,436,305, 5,451,649, 5,496,781, 5,498,581, 5,541,272, 5,554,795, 5,563,284, 5,565,592, 5,571,880, 5,594,078, 5,631,203, 5,631,335, 5,654,454, 5,668,230, 5,705,478, 5,705,579, 6,187,880, 6,509,427, and 6,524,987 all describe such methods. Other processes to prepare metallocene compounds that can be employed in this invention have been reported in references such as: Köppl, A. Alt, H. G. *J. Mol. Catal A*. 2001, 165, 23; Kajigaeshi, S.; Kadowaki, T.; Nishida, A.; Fujisaki, S. *The Chemical Society of Japan*, 1986, 59, 97; Alt, H. G.; Jung, M.; Kehr, G. *J. Organomet. Chem*. 1998, 562, 153-181; and Alt, H. G.; Jung, M. *J. Organomet. Chem*. 1998, 568, 87-112, each of which is incorporated by reference herein, in their entireties. Further, additional processes to prepare metallocene compounds that can be employed in this invention have been reported in: *Journal of Organometallic Chemistry*, 1996, 522, 39-54, which is incorporated by reference herein, in its entirety. The following treatises also describe such methods: Wailes, P. C.; Coutts, R. S. P.; Weigold, H. in *Organometallic Chemistry of Titanium, Zirconium, and Hafnium, Academic*; New York, 1974.; Cardin, D. J.; Lappert, M. F.; and Raston, C. L.; *Chemistry of Organo-Zirconium and -Hafnium Compounds*; Halstead Press; New York, 1986.

In a further aspect of the present invention, this disclosure encompasses additional methods for the synthesis of organic compounds comprising two cyclopentadienyl-type groups linked by a bridging group, which are useful ligands in preparing ansa-metallocene complexes that, in turn, can be used subsequently as catalyst components in olefin polymerizations. These methods can generally afford higher yields of the desired product than were heretofore available and can permit a range of substituents to be incorporated into the ligand and the ansa-metallocene. These additional methods for preparing organic compounds comprising two cyclopentadienyl-type groups linked by a bridging group have been disclosed in U.S. Pat. No. 7,064,225, which is incorporated by reference herein in its entirety.

In this aspect of this invention, a method is provided for the synthesis of compounds comprising linked cyclopentadienyl and fluorenyl groups, including substituted analogs thereof, which are precursors to ansa-metallocenes comprising bridged cyclopentadienyl and fluorenyl ligands. However, this method is also applicable to ligands comprising linked cyclopentadienyl and indenyl groups, indenyl and fluorenyl groups, two cyclopentadienyl groups, two indenyl groups, or two fluorenyl groups. This invention is specifically illustrated by the disclosure and examples of U.S. Pat. No. 7,064,225 for preparing linked cyclopentadienyl and fluorenyl groups and ansa-metallocenes comprising bridged cyclopentadienyl and fluorenyl ligands. This method utilized a fulvene compound, which can be a fulvene that is purified according to the purification methods and/or prepared according to the preparative methods of this disclosure. In this aspect, for example, this invention provides a new high-yield method for making the metallocene, (5-cyclopentadienyl)[5-(2,7-di-tert-butylfluorenyl)]hex-1-ene zirconium dichloride, as well as its parent ligand, (5-cyclopentadienyl)[5-(2,7-di-tert-butylfluorenyl)]hex-1-ene. However, many variations in the substitution patterns for this ligand and ansa-metallocene are possible, as disclosed herein.

In one aspect, this invention also provides a method for making a compound of the formula

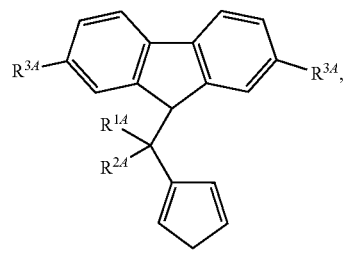

(I)

and isomers thereof, comprising:

a) contacting a compound of the formula

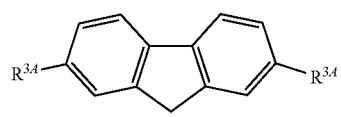

(II)

and an alkyl lithium reagent in an ethereal solvent to form a first mixture, wherein compound II is substantially deprotonated to form Li$^+$[II$^-$];

b) rapidly combining the first mixture with a fulvene compound of the formula

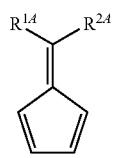

(III)

to form a second mixture, wherein either Li$^+$[II$^-$] or compound III is optionally a limiting reagent, and wherein the limiting reagent, if present, has substantially reacted; and c) contacting the second mixture with a proton source to form a third mixture comprising

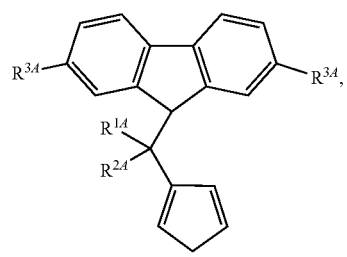

(I)

and isomers thereof;

wherein $R^{1A}$ and $R^{2A}$ independently are hydrogen or an aliphatic or substituted aliphatic group having from 1 to about 20 carbon atoms; and wherein each $R^{3A}$ independently is hydrogen or an aliphatic or substituted aliphatic group having from 1 to about 20 carbon atoms.

Possible substituents for $R^{1A}$, $R^{2A}$, and $R^{3A}$ are provided herein. Typically, compound I is formed in at least about 85% yield, at least about 90% yield, or at least about 95% yield. Thus, in this method, the fulvene compound of the formula III used to form a second mixture can be a fulvene that is purified and/or prepared according to this disclosure.

For example, compounds of the formula I that can be prepared using this invention include the compound of the formula

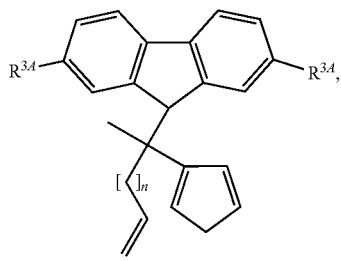

which can be prepared as disclosed herein using the precursors

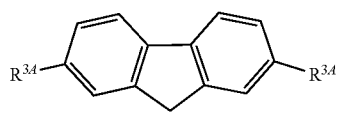

(II)

and compound III having the specific formula

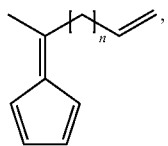

wherein $R^{3A}$ can be typically H, t-butyl, i-propyl, n-propyl, ethyl, or methyl, and wherein n is an integer from 1 to about 6.

Further to this aspect of the invention, the concentration of the $Li^+[II^-]$ reagent in the first mixture prior to rapidly combining the first mixture with III, can be from about 0.5 M to about 1.8 M. Alternatively, the concentration of the $Li^+[II^-]$ reagent in the first mixture prior to rapidly combining the first mixture with III, can be from about 0.7 M to about 1.5 M.

The alkyl lithium reagent of this aspect of the invention can comprise MeLi, n-BuLi, t-BuLi, n-hexylLi, $LiCH_2SiMe_3$, $LiCH_2Ph$, $LiCH_2CMe_3$, or any combination thereof. In this aspect, compound II and the alkyl lithium reagent can react to form $Li^+[II^-]$ in at least about 95% yield. Generally, the first mixture can be combined with III over a time period of less than about 5 minutes, less than about 3 minutes, less than about 1 minute, less than about 30 seconds, or less than about 15 seconds.

In a further aspect, the proton source can comprise water, an aqueous acid, an aqueous ammonium salt, or any combination thereof. Further, step a can be initiated from about 0° C. to about −100° C. For example, step a can be initiated at about −78° C. In yet another aspect, step a can be conducted from about room temperature to about −78° C. Step b, in another aspect, can be initiated from about 0° C. to about −100° C. For example, step b can be initiated at about −78° C. In still another aspect, step b can be conducted from about room temperature to about −78° C.

Still another aspect of this disclosure provides that the limiting reagent of step b in the above process can be present in at least about 50% the mole fraction of the non-limiting reagent. In a further aspect of this invention, at least about 90% of the limiting reagent of step b can react, or at least about 95% of the limiting reagent of step b can react. Yet another aspect of this disclosure is that compound I is formed in at least about 85% yield, at least about 90% yield, or at least about 95% yield.

In another aspect, this invention provides a method of making a compound of the formula

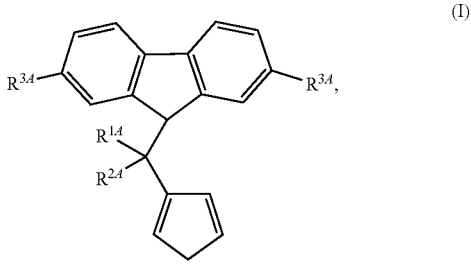

(I)

and isomers thereof, comprising:

a) providing a source of a fluorenyl anion having the formula

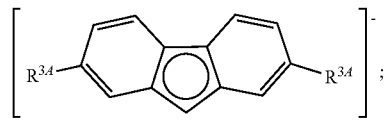

b) rapidly combining the source of the fluorenyl anion with a fulvene compound of the formula

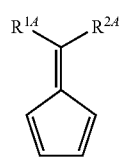

(III)

to form a mixture, wherein either the source of the fluorenyl anion or compound III is optionally a limiting reagent, and wherein the limiting reagent, if present, has substantially reacted; and c) contacting the mixture with a proton source to form

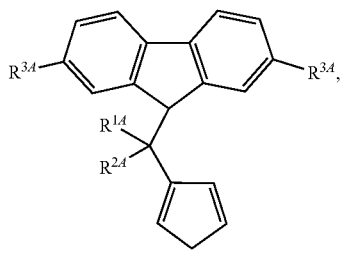

and isomers thereof, wherein $R^{1A}$ and $R^{2A}$ independently are hydrogen or an aliphatic or substituted aliphatic group having from 1 to about 20 carbon atoms; and wherein each $R^{3A}$ independently is hydrogen or an aliphatic or substituted aliphatic group having from 1 to about 20 carbon atoms. In this aspect, for example, the source of the fluorenyl anion having the formula

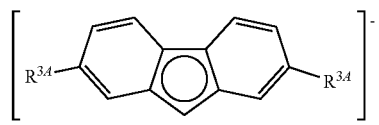

can typically comprise lithium, sodium, potassium, magnesium, calcium, or a combination thereof, in addition to comprising the fluorenyl anion. For example, the source of the fluorenyl anion having the formula

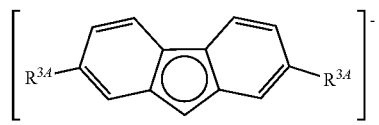

can typically comprise a salt of the fluorenyl anion comprising lithium, sodium, potassium, magnesium, calcium, or a combination thereof.

The ethereal solvent used in this method, can be independently selected from a range of ethereal solvents, including, but not limited to, dimethyl ether, diethyl ether, diisopropyl ether, di-n-propyl ether, di-n-butyl ether, methyl t-butyl ether, diphenyl ether, THF, 1,2-dimethoxyethane, or any combination thereof.

In another aspect of the invention, the rapid combination of the ethereal solution of the fluorenyl component $Li^+[II^-]$ and the fulvene compound III, is typically carried out over a time period of less than about 1 minute. This combination time for the fluorenyl and the fulvene compounds is different than the total contact time between these compounds, prior to proceeding to the subsequent step in the process. The combination time describes the elapsed time over which the addition of the fulvene to the ethereal solution of the fluorenyl, or alternatively, the addition of the ethereal solution of fluorene compound to the fulvene, is initiated and completed.

This method can further comprise isolating compound I. For example, the method of this invention can further comprise removing the volatile components from the third mixture to provide a residue comprising I, optionally triturating the residue with a solvent in which I is substantially insoluble and III is soluble, and isolating I. Examples of solvents that are useful in this trituration include, but are not limited to, alcohols having up to about 8 carbon atoms, examples of which include, but are not limited to methanol, ethanol, i-propanol, n-propanol, n-butanol, sec-butanol, t-butanol, 1-hexanol, 2-hexanol, 3-hexanol, any mixture thereof, or any combination thereof.

In a further aspect of this invention, a method is provided for making an ansa-metallocene compound of the formula

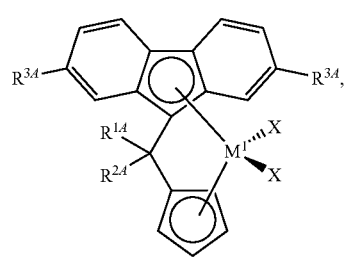

comprising:

a) contacting a compound of the formula

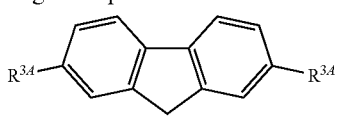

and a first alkyl lithium reagent in a first ethereal solvent to form a first mixture, wherein compound II is substantially deprotonated to form $Li^+[II^-]$;

b) rapidly combining the first mixture with a fulvene compound of the formula

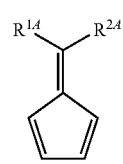

to form a second mixture, wherein the limiting reagent has substantially reacted;

c) contacting the second mixture with a proton source to form a third mixture comprising

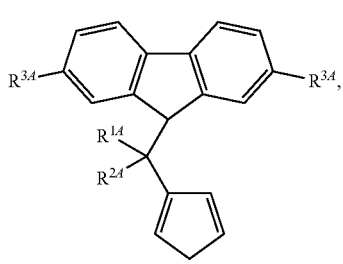

including isomers thereof, in at least about 85% yield;

d) removing the volatile components from the third mixture to provide a residue comprising I;

e) optionally triturating the residue with a solvent in which I is substantially insoluble and III is soluble to provide I, followed by isolation of I;

f) contacting the I with from about 2 to about 2.5 molar equivalents of a second alkyl lithium reagent in a second ethereal solvent to form a fourth mixture, wherein the I is substantially deprotonated to form $Li^+_2[I^{2-}]$;

g) contacting the fourth mixture with $M^1X_4$ and an optional hydrocarbon cosolvent to form a fifth mixture comprising

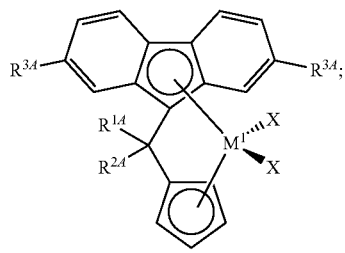

(IV)

h) removing the volatile components from the fifth mixture to provide IV in at least about 80% yield;

i) optionally washing the IV in a non-polar solvent;

j) optionally extracting the IV with a polar solvent followed by removing the volatiles from the polar solvent solution to provide IV; and k) optionally crystallizing the IV from an aromatic solvent;

wherein:

$R^{1A}$ and $R^{2A}$ are independently selected from an aliphatic or substituted aliphatic group having from 1 to about 20 carbon atoms, or hydrogen; and $R^{3A}$, in each instance, is independently selected from an aliphatic or substituted aliphatic group having from 1 to about 20 carbon atoms, or hydrogen;

$M^1$ is Zr or Hf; and

X is Cl, Br, or I.

It was found that yields of the metallocene were improved when the volatile components were removed from the fifth mixture to provide IV.

This method can also be used to prepare a zirconocene analog having the structure

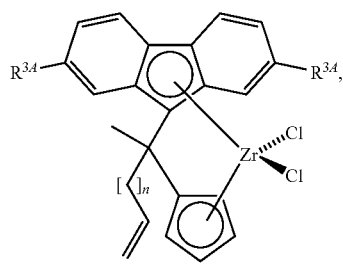

according to the method disclosed herein, wherein compound I has the formula

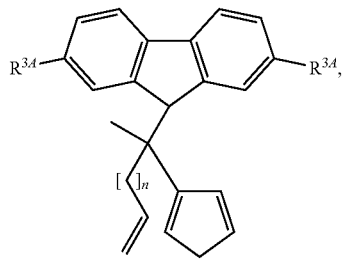

compound If has the formula

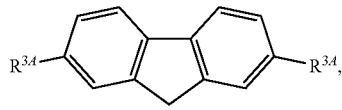

and compound III has the formula

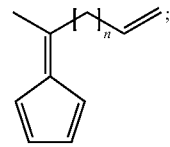

wherein:

$R^3$ is H, t-butyl, i-propyl, n-propyl, ethyl, or methyl; and n is an integer from 1 to about 6.

In one aspect, the first and second alkyl lithium reagents can be selected independently from, for example, MeLi, n-BuLi, t-BuLi, n-hexylLi, $LiCH_2SiMe_3$, $LiCH_2Ph$, $LiCH_2CMe_3$, or any combination thereof. In a further aspect, the first mixture can be combined with III over a time period of less than about 3 minutes, over a time period of less than about 1 minute, or over a time period of less than about 30 seconds. Moreover, the compound II and the first alkyl lithium reagent can react to form $Li^+[II^-]$ in at least about 95% yield, and the fourth mixture can comprise $Li^+_2[I^{2-}]$ in at least about 90% yield.

In a further aspect of the invention, the rapid combination of a fluorenyl component $Li^+[II^-]$ with a fulvene component III is typically carried out over a time period of less than about 5 minutes, less than about 3 minutes, less than about 1 minute, or less than about 15 seconds. This combination time for the fluorenyl and the fulvene compounds is different than the total contact time between these compounds, prior to proceeding to the subsequent step in the process.

The first and second ethereal solvents used in the preparation of the metallocene can be independently selected from a range of ethereal solvents, including, but not limited to, dimethyl ether, diethyl ether, diisopropyl ether, di-n-propyl ether, di-n-butyl ether, methyl t-butyl ether, diphenyl ether, THF, 1,2-dimethoxyethane, or any combination thereof.

This method of preparing the metallocene, which comprises removing the volatile components from the third mixture to provide a residue comprising I, can also optionally comprise triturating the residue with a solvent in which I is substantially insoluble and III is soluble to provide I, followed by isolation of I. Examples of solvents that are useful in this trituration include, but are not limited to, alcohols having up to about 8 carbon atoms, examples of which include, but are not limited to methanol, ethanol, i-propanol, n-propanol, n-butanol, sec-butanol, t-butanol, 1-hexanol, 2-hexanol, 3-hexanol, any mixture thereof, or any combination thereof. In one aspect, the optional hydrocarbon cosolvent and the non-polar solvent can be selected independently from butane, pentane, cyclopentane, hexane, heptane, cyclohexane, methyl cyclopentane, octane, or any combination thereof. The polar solvent disclosed in the method can be selected from, for example, $CHCl_3$, $CH_2Cl_2$, 1,2-dichlorethane, or any combination thereof. Further, the aromatic solvent can be selected from benzene, toluene, xylene, mesitylene, ethyl benzene, anisole, aniline, or any combination thereof.

In yet another aspect of this invention, this disclosure provides a method of isolating a compound of the formula $C_4R^3_4C=CR^1R^2$ and methods of making compounds of the formulas: $C_4R^6_4C=CR^4CH_2R^5$; $C_4R^6_4CHCR^4(CH_2R^5)(QH)$, wherein Q is a cyclopentadienyl, an indenyl, or a fluorenyl; and

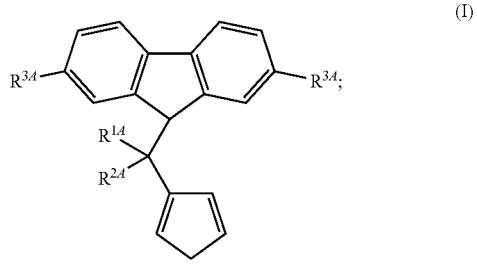

(I)

as described above. As disclosed herein, $R^4$, $R^5$ and $R^6$, independently, can be a substituted hydrocarbyl groups, and $R^{1A}$, $R^{2A}$, $R^{3A}$, and $R^{4A}$, independently, can be a substituted aliphatic group. Moreover, Q can be a substituted cyclopentadienyl, a substituted indenyl, or a substituted fluorenyl, in which any substituent on Q can be selected independently from $R^{4A}$.

In this aspect, any substituent on $R^4$, $R^5$, $R^6$, $R^{1A}$, $R^{2A}$, $R^{3A}$, or $R^{4A}$, can be selected independently from an aliphatic group, an aromatic group, a cyclic group, a combination of aliphatic and cyclic groups, an oxygen group, a sulfur group, a nitrogen group, a phosphorus group, an arsenic group, a carbon group, a silicon group, a germanium group, a tin group, a boron group, an aluminum group, or hydrogen, and the like. These substituents can be further described herein as follows. In each of the examples presented herein, unless otherwise specified, R is independently selected from H, an aliphatic group, an aromatic group, or a cyclic group, having from 1 to about 20 carbon atoms.

Examples of aliphatic groups, in each instance, include but are not limited to, hydrocarbyls such as paraffins and olefins having from 1 to about 20 carbon atoms. Thus, aliphatic groups, in each instance, include, but are not limited to, an alkyl group, a cycloalkyl group, an alkenyl group, a cycloalkenyl group, an alkynyl group, an alkadienyl group, a cyclic group, and the like, and includes all branched and linear analogs thereof, in each instance having from 1 to about 20 carbon atoms. For example, aliphatic groups as used herein include methyl, ethyl, propyl, n-butyl, tert-butyl, sec-butyl, isobutyl, amyl, isoamyl, hexyl, cyclohexyl, heptyl, octyl, nonyl, decyl, dodecyl, 2-ethylhexyl, pentenyl, butenyl, and the like. Aliphatic groups include alkenyl groups, alkynyl groups, alkadienyl groups, and the like, having from 1 to about 20 carbon atoms, including any regioisomer thereof.

Examples of aromatic groups include, but are not limited to, phenyl, naphthyl, anthracenyl, and the like.

Examples of cyclic groups include, but are not limited to, cycloparaffins, cycloolefins, cycloacetylenes, arenes such as phenyl, bicyclic groups and the like, including substituted derivatives thereof, having from 3 to about 20 carbon atoms.

The combination of aliphatic and cyclic groups are groups comprising an aliphatic portion and a cyclic portion, examples of which include, but are not limited to, groups such as: $-(CH_2)_mC_6H_qR_{5-q}$ wherein m is an integer from 1 to about 10, and q is an integer from 1 to 5, inclusive; $-(CH_2)_mC_6H_qR_{11-q}$ wherein m is an integer from 1 to about 10, and q is an integer from 1 to 11, inclusive; or $-(CH_2)_mC_5H_qR_{9-q}$ wherein m is an integer from 1 to about 10, and q is an integer from 1 to 9, inclusive.

Oxygen groups are oxygen-containing groups, examples of which include, but are not limited to, alkoxy or aryloxy groups (—OR), —$OSiR_3$, and the like, wherein R in each instance is selected from alkyl, cycloalkyl, or aryl having from 1 to about 20 carbon atoms. Examples of alkoxy or aryloxy groups (—OR) groups include, but are not limited to, methoxy, ethoxy, propoxy, butoxy, phenoxy, substituted phenoxy, and the like.

Sulfur groups are sulfur-containing groups, examples of which include, but are not limited to, —SR, wherein R in each instance is selected from alkyl, cycloalkyl, or aryl, having from 1 to about 20 carbon atoms.

Nitrogen groups are nitrogen-containing groups, which include, but are not limited to, —$NR_2$, wherein R in each instance is selected from alkyl, cycloalkyl, or aryl, having from 1 to about 20 carbon atoms.

Phosphorus groups are phosphorus-containing groups, which include, but are not limited to, —$PR_2$, wherein R in each instance is selected from alkyl, cycloalkyl, or aryl, having from 1 to about 20 carbon atoms.

Arsenic groups are arsenic-containing groups, which include, but are not limited to, —$AsR_2$, wherein R in each instance is selected from alkyl, cycloalkyl, or aryl, having from 1 to about 20 carbon atoms.

Carbon groups are carbon-containing groups, which include, but are not limited to, alkyl halide groups that include halide-substituted alkyl groups with 1 to about 20 carbon atoms, aralkyl groups with 1 to about 20 carbon atoms, including alkyl, cycloalkyl, aryl, aralkyl, substituted alkyl, substituted aryl, or substituted aralkyl groups.

Silicon groups are silicon-containing groups, which include, but are not limited to, silyl groups such alkylsilyl groups, arylsilyl groups, arylalkylsilyl groups, siloxy groups, and the like, which in each instance have from 1 to about 20 carbon atoms. For example, silicon groups include trimethylsilyl and phenyloctylsilyl groups.

Germanium groups are germanium-containing groups, which include, but are not limited to, germyl groups such alkylgermyl groups, arylgermyl groups, arylalkylgermyl groups, germyloxy groups, and the like, which in each instance have from 1 to about 20 carbon atoms.

Tin groups are tin-containing groups, which include, but are not limited to, stannyl groups such alkylstannyl groups, arylstannyl groups, arylalkylstannyl groups, stannoxy (or "stannyloxy") groups, and the like, which in each instance have from 1 to about 20 carbon atoms.

Boron groups are boron-containing groups, which include, but are not limited to, —$BR_2$, wherein R in each instance is selected from alkyl, cycloalkyl, or aryl, having from 1 to about 20 carbon atoms.

Aluminum groups are aluminum-containing groups, which include, but are not limited to, —AlR$_2$, wherein R in each instance is selected from alkyl, cycloalkyl, or aryl, having from 1 to about 20 carbon atoms.

The present invention is further illustrated by the following examples, which are not to be construed in any way as imposing limitations upon the scope thereof. On the contrary, it is to be clearly understood that resort may be had to various other aspects, features, embodiments, modifications, and equivalents thereof which, after reading the description herein, may suggest themselves to one of ordinary skill in the art without departing from the spirit of the present invention or the scope of the appended claims.

EXAMPLES

Generally, the solvents used in the following Examples were dried and distilled using standard methods. The Nuclear Magnetic Resonance (NMR) spectra reported herein were obtained on a Varian Mercury Plus 300 NMR spectrometer operating at 300 MHz for $^1$H NMR (CDCl$_3$ solvent, referenced against the peak of residual CHCl$_3$ at 7.24 ppm) and 75 MHz for $^{13}$C NMR (CDCl$_3$ solvent, referenced against central line of CHCl$_3$ at 77.00 ppm).

Pentatriacontanone, ([CH$_3$(CH$_2$)$_{16}$]$_2$CO) was obtained from Alfa Aesar and was used as received.

Cyclopentadienyl magnesium chloride (CpMgCl) was purchased from Boulder Scientific as solution in THF. CpMgCl can also be prepared according to the procedure detailed in U.S. Pat. No. 6,175,027. U.S. Pat. No. 6,175,027 also provides a general description of cyclopentadienyl Grignard synthesis methods. A method for preparing CpMgX is also reported by Stille and Grubbs in *J. Org. Chem.*, (1989), 54, 441. Dicyclopentadienyl magnesium could be prepared according to Duff, Hitchcock, Lappert, and Taylor, *J. Organometal. Chem.* (1985), 293, 271.

Example 1

Preparation of 6,6-diheptadecylpentafulvene

Pentatriacontanone, ([CH$_3$(CH$_2$)$_{16}$]$_2$CO) 46.0 g (90.7 mmol), was slurried in 100 mL of dry THF and stirred vigorously. A solution of cyclopentadienylmagnesium chloride in THF, 125 mL (125 mmol), was added dropwise. After about 30 minutes most of the ketone had dissolved. Stirring was continued for 2 hours and then the mixture was refluxed for 2 hours. Stirring was further continued for about 16 hours, after which time the orange solution was cooled in an ice bath, and a mixture of 15 mL of concentrated HCl(aq) and 100 mL of water was added. The resulting mixture was extracted with 200 mL of n-pentane and the organic layer was washed with 3×100 mL of water and dried over sodium sulfate. After filtration, the solvent was removed from the filtrate in vacuo to provide a yellow paste. Both $^1$H and $^{13}$C NMR spectra of this paste showed the product to be a mixture of 6,6-diheptadecylpentafulvene and isomeric alkenylcyclopentadienes, along with residual THF, 55.1 grams. The yield of the alkenylcyclopentadienes was estimated from the $^1$H NMR spectrum to be about 51%. FIG. 1 illustrates the $^1$H NMR spectrum of the crude reaction product arising from the reaction of CpMgCl and [CH$_3$(CH$_2$)$_{16}$]$_2$CO in THF.

Example 2

Attempted Purification of 6,6-diheptadecylpentafulvene Using Chromatography

The mixture of 6,6-diheptadecylpentafulvene and isomeric alkenylcyclo-pentadienes prepared according to Example 1 was dissolved in 200 mL of n-pentane and passed through a short column (15 cm×4 cm) of Davison Grade 62 silica. The resulting filtrate was concentrated under vacuum to provide a yellow solid. Both $^1$H NMR and $^{13}$C NMR spectroscopy revealed that the residual THF was removed, but the isomeric alkenylcyclopentadienes were not removed. The yield of the alkenylcyclopentadienes was estimated from the $^1$H NMR spectrum to be about 54%, with 44.6 g of reaction product recovered. FIG. 2 illustrates the $^1$H NMR spectrum of the product arising from the reaction of CpMgCl and [CH$_3$(CH$_2$)$_{16}$]$_2$CO in THF, following chromatography as described in this example.

Example 3

Purification of 6,6-diheptadecylpentafulvene

A solution of 7.46 g (50 mmol) of 4-(N,N-dimethylamino) benzaldehyde and 10 mL of pyrrolidine (120 mmol) in 50 mL of methanol and 70 mL of methylene chloride was degassed and added to 44.5 grams of crude diheptadecylpentafulvene. This mixture was stirred for about 20 h to give a dark red mixture. A 25 mL portion of glacial acetic acid in 100 mL of water was added to this solution and the resulting mixture was extracted with 200 mL of pentane. The organic layer was washed with 3×100 mL of water, dried over magnesium sulfate, and filtered. The solvent was removed under vacuum leaving a viscous, dark red liquid. A portion of this liquid, 27.8 g, was passed through a column of Davison Grade 62 silica (30 cm×4 cm) and eluted with n-pentane. A yellow band eluted first and was well separated from a dark red band. The yellow solution collected first was concentrated under vacuum to provide a yellow oil, 8.5 g. Both $^1$H NMR and $^{13}$C NMR spectra of this oil indicated the oil was pure 6,6-diheptadecylpentafulvene. Chromatography of a second batch of dark red liquid according to the above technique provided more pure 6,6-diheptadecylpentafulvene and brought the total yield to 14.2 g. FIG. 3 illustrates the $^1$H NMR spectrum of the pure 6,6-diheptadecylpentafulvene product.

Throughout this disclosure, unless otherwise stated, any recitation of a range or a number is inclusive of the end members of that range. For example, the recitation that an alcohol has up to 4 carbon atoms is intended to refer to an alcohol having 1, 2, 3, or 4 carbon atoms. Further, unless otherwise stated, the recitation that n is an integer from 6 to 16 is intended to include the end members 6 and 16 in the possible values for integer n.

Although any methods, devices, and materials similar to or equivalent to those described herein can be used in the practice or testing of the invention, the typical methods, devices and materials are herein described.

All publications and patents mentioned in this disclosure are incorporated herein by reference in their entireties, for the purpose of describing and disclosing, for example, the constructs and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

To the extent that any definition or usage provided by any document incorporated herein by reference conflicts with the definition or usage provided herein, the definition or usage provided herein controls.

For any particular compound disclosed herein, any general structure presented also encompasses all conformational isomers, regioisomers, and stereoisomers that may arise from a particular set of substituents. The general structure also encompasses all enantiomers, diastereomers, and other optical isomers whether in enantiomeric or racemic forms, as well as mixtures of stereoisomers, as the context requires.

We claim:

1. A method of isolating a fulvene from a composition comprising the fulvene and at least one cyclopentadiene-containing impurity, comprising:
   a) contacting the composition with 4-(N,N-dimethylamino)benzaldehyde, pyrrolidine, and optionally a first solvent to provide a first mixture;
   b) contacting the first mixture with an aqueous acid to provide a second mixture;
   c) extracting the second mixture with a second solvent to provide an extract, optionally concentrating the extract, and optionally drying the extract; and
   d) isolating the fulvene from the extract by chromatography;
wherein:
the fulvene has the formula

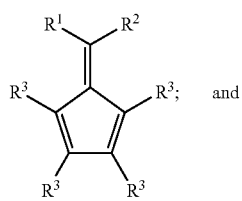

$R^1$, $R^2$, and $R^3$, in each occurrence, are independently a hydrocarbyl group having up to 20 carbon atoms, or hydrogen.

2. The method according to claim 1, wherein $R^1$ and $R^2$ are selected independently from: a) a linear or a branched alkyl group; b) a linear or a branched alkenyl group; c) an aryl group; or d) an aryl-substituted linear or branched alkyl group; any of which having up to 20 carbon atoms.

3. The method according to claim 1, wherein $R^3$, in each occurrence, is selected independently from: a) a linear or a branched alkyl group having up to 12 carbon atoms; or b) hydrogen.

4. The method according to claim 1, wherein $R^1$ and $R^2$ are, independently, an alkyl group having from 1 to 18 carbon atoms.

5. The method according to claim 1, wherein the fulvene has the formula:

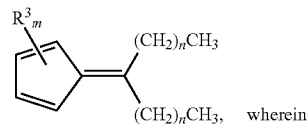

$R^3$, in each occurrence, is independently a linear or a branched alkyl group having up to 6 carbon atoms;
m is 0, 1, 2, 3, or 4; and
n is an integer from 1 to 16.

6. The method according to claim 1, wherein the fulvene has the formula:

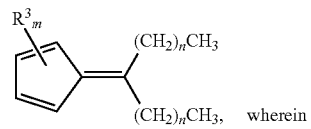

$R^3$, in each occurrence, is independently a linear or a branched alkyl group having up to 6 carbon atoms;
m is 0, 1, 2, 3, or 4; and
n is an integer from 6 to 16.

7. The method according to claim 1, wherein the at least one cyclopentadiene-containing impurity is

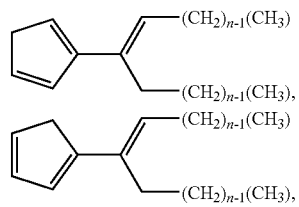

or a combination thereof, wherein n is an integer from 1 to 16.

8. The method according to claim 1, wherein the at least one cyclopentadiene-containing impurity is

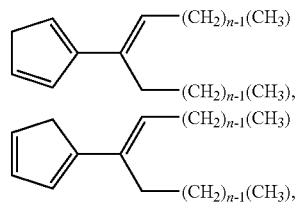

or a combination thereof, wherein n is an integer from 6 to 16.

9. The method according to claim 1, wherein the fulvene has the formula $C_4H_4C = C(CH_2)_{16}CH_3$.

10. The method according to claim 1, wherein the first solvent is a mixture of methylene chloride and an alcohol having up to 4 carbon atoms.

11. The method according to claim 1, wherein the first solvent is a mixture of methylene chloride and methanol.

12. The method according to claim 1, wherein the second solvent is pentane, hexane, heptane, or any combination thereof.

13. The method according to claim 1, wherein the aqueous acid is acetic acid, trifluoroacetic acid, formic acid, hydrochloric acid, phosphoric acid, sulfuric acid, nitric acid, or any combination thereof.

14. The method according to claim 1, wherein the extract is concentrated prior to isolating the fulvene from the extract by chromatography.

15. The method according to claim 1, wherein the extract is dried prior to isolating the fulvene from the extract by chromatography.

16. A method of isolating a fulvene from a composition comprising the fulvene and at least one cyclopentadiene-containing impurity, comprising:
    a) contacting the composition with 4-(N,N-dimethylamino)benzaldehyde, pyrrolidine, and optionally a first solvent to provide a first mixture;
    b) contacting the first mixture with an aqueous acid to provide a second mixture;
    c) extracting the second mixture with a second solvent to provide an extract, optionally concentrating the extract, and optionally drying the extract; and
    d) isolating the fulvene from the extract by chromatography;

wherein:
    the fulvene has the formula $C_4H_4C=C[(CH_2)_{16}CH_3]_2$.

17. The method according to claim 16, wherein the first solvent is a mixture of methylene chloride and an alcohol having up to 4 carbon atoms.

18. The method according to claim 16, wherein the first solvent is a mixture of methylene chloride and methanol.

19. The method according to claim 16, wherein the second solvent is pentane, hexane, heptane, or any combination thereof.

20. The method according to claim 16, wherein the aqueous acid is acetic acid, trifluoroacetic acid, formic acid, hydrochloric acid, phosphoric acid, sulfuric acid, nitric acid, or any combination thereof.

21. The method according to claim 16, wherein the extract is concentrated prior to isolating the fulvene from the extract by chromatography.

22. The method according to claim 16, wherein the extract is dried prior to isolating the fulvene from the extract by chromatography.

* * * * *